United States Patent [19]

Bogdan

[11] Patent Number: 4,790,316
[45] Date of Patent: Dec. 13, 1988

[54] SURGICAL INSTRUMENT FOR REMOVING OBJECTS FROM THE SKIN

[76] Inventor: Raymond Bogdan, 520 Burr Oak, Lake Zurich, Ill. 60047

[21] Appl. No.: 49,325

[22] Filed: May 13, 1987

[51] Int. Cl.$^4$ ............................................... A61B 17/50
[52] U.S. Cl. ....................................... 128/355; 128/305
[58] Field of Search ........................ 128/314, 355, 305

[56] References Cited

U.S. PATENT DOCUMENTS 1,138,967  5/1915  Metzger ................................. 128/355

FOREIGN PATENT DOCUMENTS 9801  of 1898  United Kingdom ................. 128/353

Primary Examiner—Michael H. Thaler
Attorney, Agent, or Firm—Douglas B. White

[57] ABSTRACT

Generally there is provided an improved surgical tool or instrument which is designed to be inserted in the skin to penetrate to the site of an imbedded object, catch the object and pull it to the surface. This instrument comprises an elongated shaft having a handle portion and an operative end projecting substantially transverse thereto. The tip of the operative end includes a point directed toward the handle portion to catch the imbedded object on the withdrawal but to pass by the object on the insertion. Additionally, there is provided side edges on the shaft arranged to slice the skin during insertion to allow a cut only as large as necessary to penetrate the tool. Similarly, a further feature provides edges on the tip portion of the operative end to cut skin as necessary during extraction to open a passage only as large as necessary to remove the tool and the imbedded object. Operation of the instrument is improved with a heel formed at the transition between the shaft and the operative end, and used to press skin away from and expose the imbedded object.

3 Claims, 3 Drawing Sheets

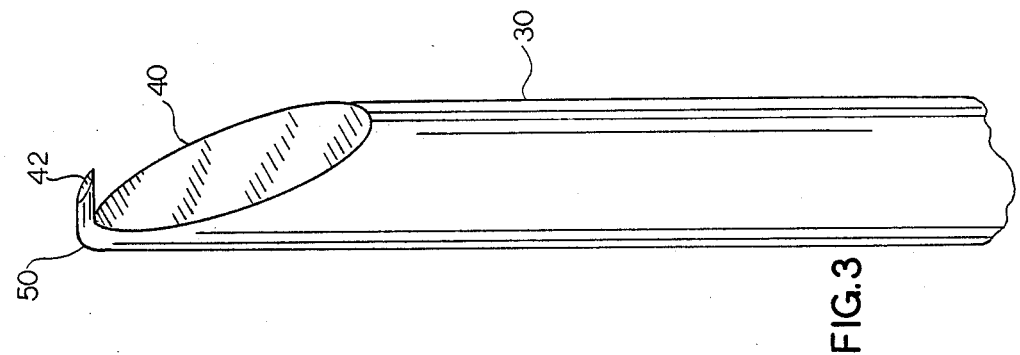
FIG. 3
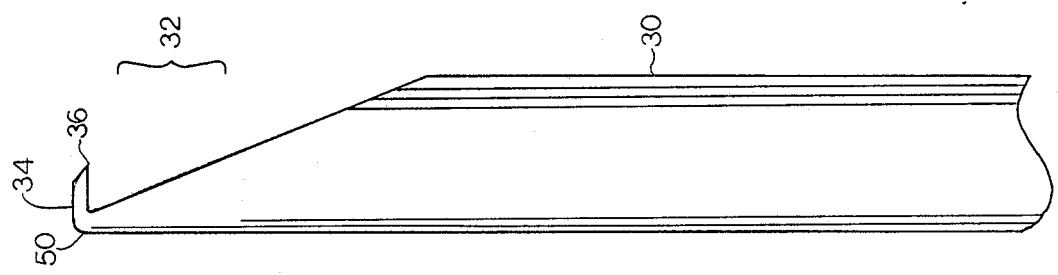
FIG. 2
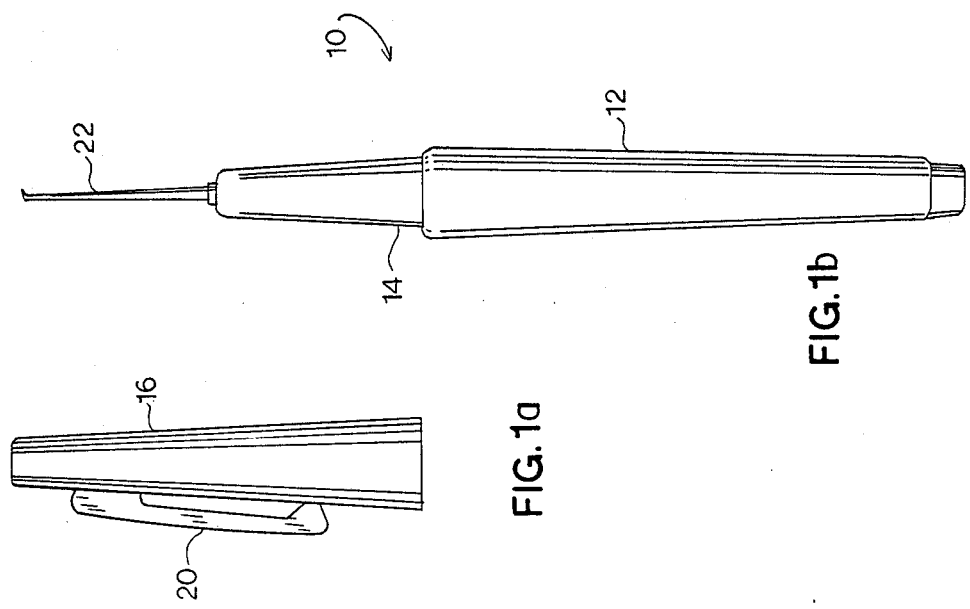
FIG. 1a
FIG. 1b

SURGICAL INSTRUMENT FOR REMOVING OBJECTS FROM THE SKIN

BACKGROUND OF THE INVENTION

1. Field of the Invention

The present invention relates generally to surgical instruments or tools for use in removing foreign objects or the like from the skin. More particularly, the invention relates to improvements in surgical tools used for removal of splinters or ingrown hairs which function efficiently and effectively to remove the object without major damage to the local area surrounding the foreign object.

2. Description of the Prior Art

Prior methods for extracting splinters or ingrown hairs have been limited principally to the familiar tweezer method and this requires the individual to first expose the object and then to penetrate deep enough into the skin to enable one to surround and grab the object with the tweezer. Undoubtably, the trauma to the area local to the operation is usually great and this is even more pronounced when one is attempting to remove ingrown hairs where no break in the skin is available through which to access the object. Recent developments in the art for assisting the removal process have been focused on the aspect of removing overlying skin layers to expose the object. In U.S. Pat. No. 4,570,613 there is described such an improvement where a razor blade style of tool is described and which is used to progressively slice layers of skin away. This continues until the tool has cut deep enough to contact the object, whereupon the tool slices into the object to thereby grab it and pull it out of the skin. This device, unfortunately, can create a large crater in the skin of an individual, therefore creating and increasing the trauma and disfigurement associated with the removal. While alternatives have been found by using ordinary household tools to poke, cut and grab at splinters and ingrown hairs, no practical alternative has been presented.

Accordingly, it is a principal object of the present invention to provide an improved surgical tool capable of removing a splinter or ingrown hair or the like which minimizes trauma to the area local to the site.

It is yet a further object to provide a tool which is cabable of producing slight cuts in the skin when necessary and only to the extent required to allow insertion of the tool.

Another object of the invention is to provide a tool which is capable of producing slight cuts in the skin when necessary and only to the extent required to allow withdrawal of the tool and object.

Yet another object of the invention is to provide a method of removal of objects from the skin which is efficient and which does not cause gross damage to the skin, even where the skin has grown over the object preventing direct and easy access.

Other objects and advantages of the present invention will become apparent upon reference to the following detailed description and to the drawings, and upon reference to the Claims.

SUMMARY OF THE INVENTION

Generally there is provided an improved surgical tool or instrument which is designed to be inserted into the skin to penetrate to the site of an imbedded object, to catch the object and to pull it to the surface. This instrument is designed principally of an elongated shaft having a handle portion and an operative end projecting substantially transverse thereto. Additionally, there is provided on the tip of the operative end, a point directed toward the handle portion to catch the imbedded object on the withdrawal, but to pass by the object on the insertion. In yet another feature of the invention there is provided side edges on the shaft arranged to slice the skin during insertion to allow a cut only as large as necessary to penetrate the tool. Similarly, a further feature provides edges on the tip portion of the operative end to cut skin as necessary during extraction to open a passage only as large as necessary to remove the tool and the imbedded object. Finally, in yet another feature there is provided a heel portion of the tool formed at the transition between the shaft and the operative end. This heel is used to press skin away from the imbedded object and to expose the object. When used in conjunction with the edges on the shaft, very little damage is done to the skin during a removal process.

BRIEF DESCRIPTION OF THE DRAWINGS

FIG. 1 depicts a perspective view of the preferred embodiment of the present invention packaged such as to be capped to prevent damage or contamination to the operative end of the surgical instrument, where FIG. 1a depicts the cap portion and FIG. 1b depicts the surgical tool and handle.

FIG. 2 illustrates a side view of the operative end of the surgical instrument of the present invention shown in FIG. 1b, and showing in more detail the tip and point of the instrument.

FIG. 3 is a perspective view of the surgical instrument of the present invention showing the operative end and the tip portions in perspective, and further showing the cutting edges of the operative end.

DESCRIPTION OF THE PREFERRED EMBODIMENT

Figure 4A:
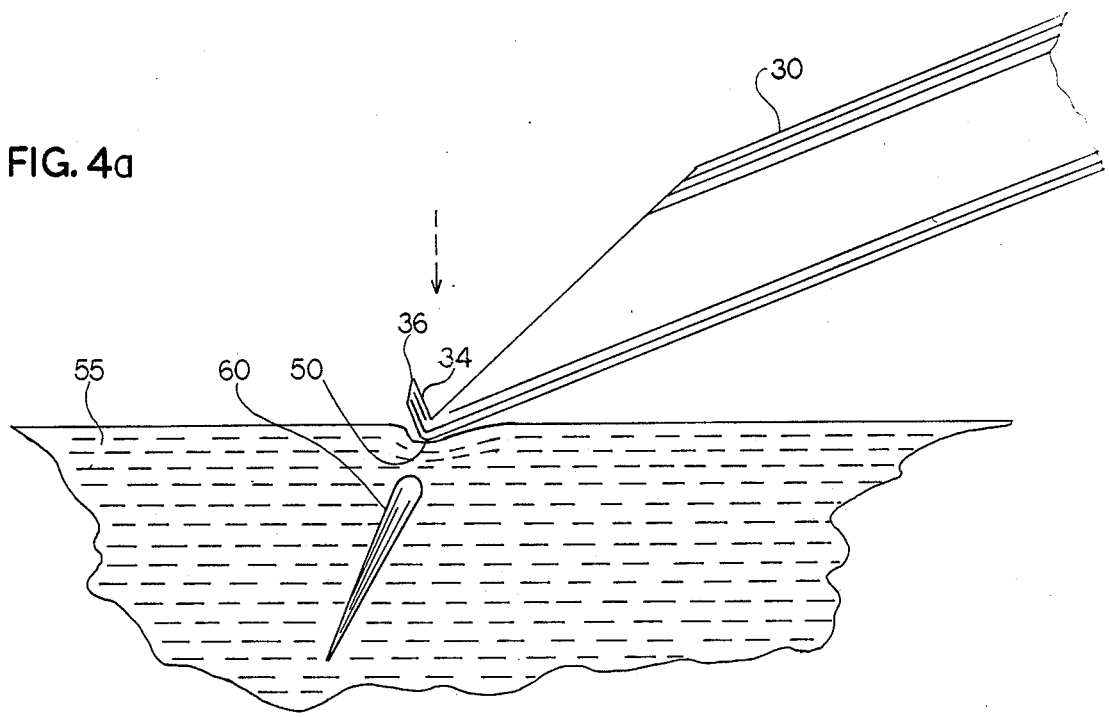
FIG. 4a is a side view of the surgical instrument of the present invention shown in use in accordance with the method of the present invention, wherein an object is imbedded in the skin of a patient and the heel of the instrument is pressing upon the skin over the imbedded object.

Turning first to FIGS. 1a and 1b there is shown a version of the preferred embodiment of the surgical instrument 10 of the invention arranged for ease in carrying and secure sanitation. Particularly, there is shown a handle portion 12 having a reduced circumference 14 at the tool end thereof. This reduced circumference portion 14 is arranged to accept a cap member 16 and to secure same in frictional contact therewith. In one form or embodiment of the invention, there is provided a clip member 20 affixed to the cap member to facilitate convenient carrying. When closed, the cap member 16 encloses the operative end 22 of the surgical tool of the present invention. This end or implement of the tool is positioned and affixed within the casing of the handle member and held securely therein to prevent motion during use.

The operative end of the surgical instrument of the invention is shown most clearly in FIGS. 2 and 3, in which there is shown an elongated shaft 30 formed to taper to a reduced dimension 32 near the tip portion 34. In one embodiment of this invention this shaft may be formed from a surgical quality wire or needle material and truncated to form the taper. This wire or needle may be installed in the handle member after forming according to methods commonly known.

A tip portion 34 is provided and formed to project substantially transverse of the elongated shaft. This tip member is arranged to exhibit a point 36 at the extremity thereof designed to catch or dig into a foreign object or ingrown hair when brought into contact therewith. In the preferred version of this instrument, this point is arranged to project toward the rear or handle portion of the instrument to allow the point to slip by the object during insertion, but to catch the object on contact during withdrawl of the instrument. As shown in the drawings this point is comprised of a truncation of the tip. Since the tip is tapered this produces a point at the extremity of the tip, and this point is operatively directed toward the handle so as to catch the object only during movement in the direction toward the handle.

In yet another but highly important feature of the invention, there is shown in FIGS. 2 and 3 sharp edges 40 defined along the operative end of the instrument to slice skin coming into contact therewith. These edges are razor sharp and lie rearwardly (toward the handle) of the tip. In this arrangement, the edges contact and cut the skin only after the skin pushes past the tip and envelopes and resists the penetration of the surgical instrument. Similarly, there are provided edges 42 at the tip portion of the instrument to aid the point in the removal of the imbedded object. This occurs due to the protrusion of the edges around the point and the nature of skin to push back or envelope the point and the imbedded object. When this happens, the edges 42 contact and cut the enveloping skin which would otherwise block removal of the tool and the imbedded object.

In another feature of the invention, there is provided a heel portion 50 formed at the transition between the tapered portion of the elongated shaft and the tip portion. This heel is smooth in character and preceeds the sharp edge portion of the tapered section of the operative end during insertion into the skin. In such an arrangement the heel will work to push the skin down and away from the imbedded object and to expose the object for removal.

Figure 4B:
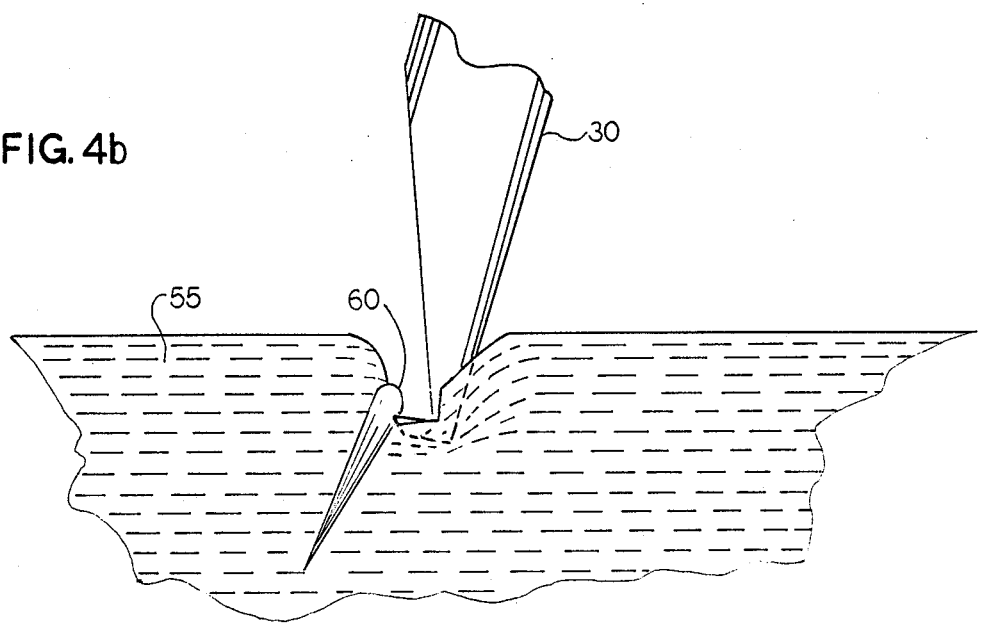
FIG. 4b is a side view of the surgical instrument of the present invention shown in use in accordance with the method of the present invention, with the instrument penetrating to the imbedded object and catching the object by the pointed tip thereof.
Figure 4C:
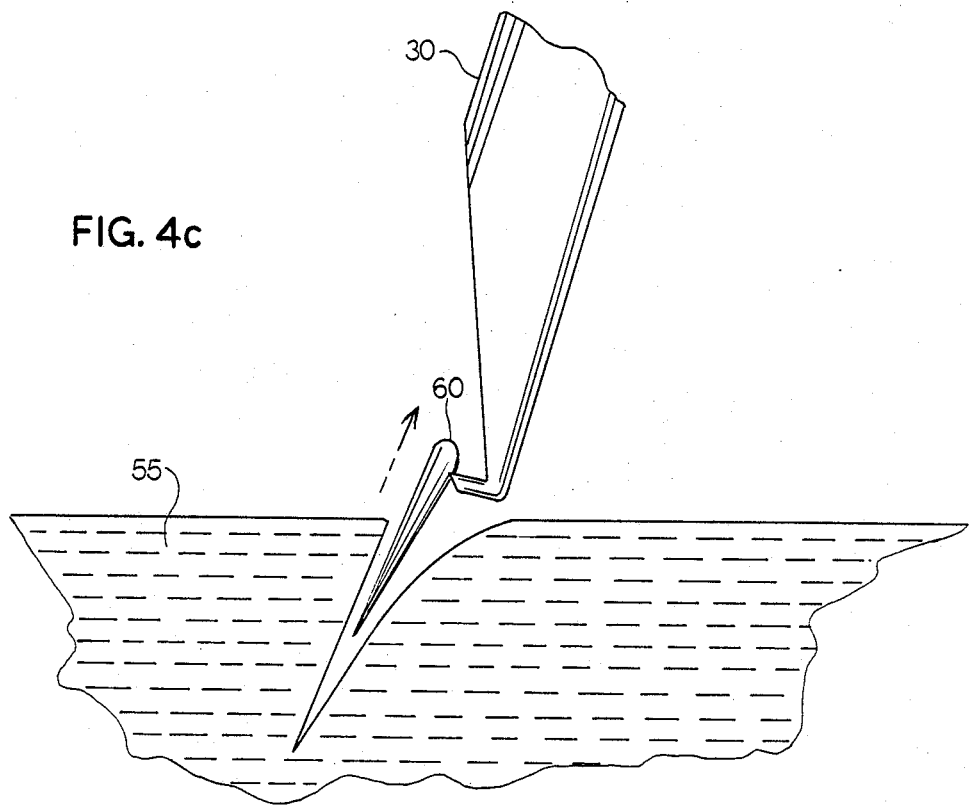
FIG. 4c is a side view of the surgical instrument of the present invention, showing the instrument pulling and removing the imbedded object in accordance with the method of the present invention.

The use and operation of the instrument of the present invention, including the function of the heel portion, the cutting edges, and the catching point is most clearly shown in FIGS. 4a, 4b, and 4c. In FIG. 4a, the operative end of the surgical instrument of the invention is shown positioned above a skin layer 55 having imbedded therein an object or ingrown hair or splinter 60. The surgical tool is pressing against the skin layer to displace the skin away from the surface and to urge the tool into the skin. Where a hole or access is left from an imbedded splinter, the tool may be inserted into the hole without penetration through the overlying skin.

FIG. 4b illustrates the position of the instrument when pressed further into the skin. At this position the tool has surgically sliced a small entry-way to the imbedded object. The sharp edges along the tapered portion of the operative end have contacted and cut the skin which has enveloped over the tool as it entered. The cutting is then limited to only the small entry needed and is a transverse cut along the same direction as the entry and removal opening for the imbedded object. This improves healing inasmuch as there is not a large jagged injury created by the operation. The instrument is further shown in FIG. 4b pressing skin away from the object by use of the heel portion to cause exposure of the imbedded object to the point of the instrument. When fully inserted the instrument may be slightly pivoted about its heel portion and the point allowed to come into contact with the object. In this position the natural pressure of the skin will urge the point into the imbedded object and urge the instrument out of the skin layer. Where the entry is close to the imbedded object, the up-turned point will allow the instrument to pass by the imbedded object during insertion, but will grab the object on withdrawl. After the point is caused to come into contact with the imbedded object and to snag the object (FIG. 4c), the object may be drawn out of the entry hole. Where the hole is not large enough, the access may be enlarged by use of the sharp edges on the point while at the same time attempting to withdraw the object.

From the foregoing description, it will be apparent that modifications can be made to the apparatus and method for using same without departing from the teaching of the present invention. Accordingly, the scope of the invention is only to be limited as necessitated by the accompanying Claims.

I claim:

1. An improved surgical tool for removing objects imbedded in skin or the like comprising:
    a handle portion;
    an elongated shaft portion having an operative end portion thereof formed to project substantially transverse thereto and forming a heel portion at the transition thereof,
    wherein said elongated shaft portion exhibits edges along opposing sides thereof proximate said heel portion arranged to slice the skin proximate contact with said heel portion during insertion of the tool; and
    a pointed tip portion generally in the form of a truncation of the operative end portion to provide a point angled toward said handle portion.

2. An improved surgical tool for removing objects imbedded in skin or the like comprising:
    a handle portion; and
    an elongated tapered cylindrical shaft, having a portion truncated along a plane, to form cutting edges along the periphery of said truncated portion, and having an operative portion formed to project substantially transverse to said shaft, said operative portion having an end portion truncated along a plane to provide a point angled toward said handle portion and forming cutting edges along said truncated end portion.

3. A method of removing an imbedded object from skin or the like comprising the steps of:
    grasping a surgical tool having an elongated shaft, a handle portion and a transversely projecting operative end thereof, said operative end having a tip point angled toward said handle portion the transition from said elongated shaft to said operative end forming a heel portion, and wherein said surgical tool further comprises cutting edges along opposing sides of said shaft proximate said heel portion and cutting edges along said operative end proximate said tip point;

pressing said heel of said tool against said skin proximate said object to urge said skin away from said object and cutting said skin with said edges along said shaft to expose said object to said tip point;

bringing said tip point into contact with said object;

catching the object with said tip point; and lifting said object from the skin and cutting skin with said edges along said operative end during the lifting of said object.

* * * * *